(12) United States Patent
Chommeloux et al.

(10) Patent No.: US 8,549,923 B2
(45) Date of Patent: Oct. 8, 2013

(54) REMOTELY ADDRESSABLE PRESSURE AND/OR TEMPERATURE MEASURING DEVICE INSTALLED IN A BIOLOGICAL MEDIUM

(75) Inventors: Luc Chommeloux, Le Cannet (FR); Philippe Menage, Vence (FR); Gerhard Heider, Le Rouret (FR)

(73) Assignee: Senseor, Sophia-Antipolis-Valbonne (FR)

( * ) Notice: Subject to any disclaimer, the term of this patent is extended or adjusted under 35 U.S.C. 154(b) by 299 days.

(21) Appl. No.: 12/990,153

(22) PCT Filed: Apr. 28, 2009

(86) PCT No.: PCT/EP2009/055103
§ 371 (c)(1),
(2), (4) Date: Oct. 28, 2010

(87) PCT Pub. No.: WO2009/133090
PCT Pub. Date: Nov. 5, 2009

(65) Prior Publication Data
US 2011/0036173 A1    Feb. 17, 2011

(30) Foreign Application Priority Data

Apr. 30, 2008    (FR) .................................. 08 02419

(51) Int. Cl.
*G01L 11/00*    (2006.01)
*A61B 5/05*    (2006.01)

(52) U.S. Cl.
USPC ................. 73/702; 73/602; 73/700; 73/704; 73/708; 600/345

(58) Field of Classification Search
None
See application file for complete search history.

(56) References Cited

U.S. PATENT DOCUMENTS

| 4,480,486 A * | 11/1984 | Meisser et al. ............. 73/861.28 |
| 4,930,350 A * | 6/1990 | Bode et al. ....................... 73/597 |
| 5,629,681 A * | 5/1997 | DuVall et al. ................. 340/665 |
| 6,053,873 A | 4/2000 | Govari et al. |
| 6,698,289 B1 * | 3/2004 | Lemcke et al. ................... 73/597 |
| 6,855,115 B2 * | 2/2005 | Fonseca et al. ............... 600/488 |
| 6,926,670 B2 * | 8/2005 | Rich et al. ..................... 600/459 |
| 7,006,858 B2 * | 2/2006 | Silver et al. ................... 600/345 |
| 7,481,771 B2 * | 1/2009 | Fonseca et al. ............... 600/486 |
| 7,699,059 B2 * | 4/2010 | Fonseca et al. ............... 128/899 |
| 7,734,343 B2 * | 6/2010 | Ransbury et al. ................. 607/4 |
| 7,769,420 B2 * | 8/2010 | Silver et al. ................... 600/345 |
| 2002/0151816 A1 | 10/2002 | Rich et al. |

FOREIGN PATENT DOCUMENTS

| WO | 0056210 | 9/2000 |
| WO | 2004014456 | 2/2004 |
| WO | 2008046850 | 4/2008 |
| WO | 2009083484 | 7/2009 |

* cited by examiner

Primary Examiner — Lisa Caputo
Assistant Examiner — Jermaine Jenkins
(74) Attorney, Agent, or Firm — Baker & Hostetler LLP

(57) ABSTRACT

A remotely interrogatable pressure and/or temperature measuring device includes at least an acoustic wave sensor including at least one resonator coupled to a first antenna element, and an interrogation system including a second antenna element for transmission and reception. The device further includes an expandable tubular structure, the structure integrating a biocompatible material, and the acoustic wave sensor is encapsulated in the biocompatible material. The second antenna element operates at frequencies above several tens of MegaHertz.

19 Claims, 7 Drawing Sheets

REMOTELY ADDRESSABLE PRESSURE AND/OR TEMPERATURE MEASURING DEVICE INSTALLED IN A BIOLOGICAL MEDIUM

CROSS-REFERENCE TO RELATED APPLICATIONS

This application is a National Stage of International patent application PCT/EP2009/055103, filed on Apr. 28, 2009, which claims priority to foreign French patent application No. FR 08 02419, filed on Apr. 30, 2008, the disclosures of which are incorporated by reference in their entirety.

FIELD OF THE INVENTION

The invention pertains to a novel type of device based on sensors, wireless and without any battery, allowing notably the measurement of arterial pressure and blood temperature, said sensor being implantable directly in a biological medium.

It concerns more precisely a passive sensor remotely interrogatable via a coupled antenna and advantageously usable in any type of organic medium exhibiting a dielectric permittivity appreciably greater than that in vacuo. Typically relevant are biological media for which it is particularly beneficial to have sensors allowing arterial pressure type pressure measurements.

BACKGROUND OF THE INVENTION

Generally, the high dielectric permittivity of biological media makes it possible to design passive sensors, notably surface wave sensors, operating at reduced electromagnetic wavelengths and thereby permitting likewise reduced antenna dimensions.

Solutions have already been proposed, notably described in the patent application BF Goodrich WO 00/56210, in which a passive surface acoustic wave (commonly dubbed "SAW") pressure sensor attached to a stent makes it possible in particular to measure blood pressure in animals or humans.

In the case considered, the mode of interrogation between the transmitter/receiver situated outside the living being and the implanted sensor is performed by inductive coupling. This mode of interrogation commonly used within the realm of sensors on passive silicon uses frequencies of possibly as high as the 13.56 MHz ISM band. Beyond these frequencies the losses: magnetic losses, eddy current losses (which increase with the square of the frequency), Joule effect losses become very significant and limit the interrogation distances to values which are no longer of interest in relation to the applications concerned.

It is however not possible to use the ISM band at 13.56 MHz to interrogate this type of device. Indeed, the size of an SAW resonator at this frequency ought to be of the order of 50 mm by 10 mm, thus ruling out implantation in the artery of a human being in particular.

SUMMARY OF THE INVENTION

In order to satisfy the compromise between sensor size (possibility of implantation) and interrogation distance, the present patent application proposes a device for measuring pressure and/or temperature using an alternative interrogation procedure based on the electromagnetic radiation of an antenna operating at frequencies above the ISM band at 13.56 MHz. By way of example this may be a system operating in the ISM band at 434 MHz. Under these conditions the size of a resonator may typically be of the order of 2.5 mm by 0.5 mm, thus making in-vivo implantation of such a device entirely possible.

In this context, the present invention proposes a novel type of implantable device comprising an SAW-based passive sensor capable of being introduced notably into an artery and thus able to provide indications regarding arterial pressure and/or blood temperature.

More precisely the subject of the present invention is a remotely interrogatable pressure and/or temperature measuring device comprising at least:

an acoustic wave sensor comprising at least one resonator coupled to a first antenna element,
an interrogation system comprising a second antenna element for transmission and reception,
characterized in that it comprises an expandable tubular structure, said structure integrating a biocompatible material and said acoustic wave sensor encapsulated in the biocompatible material and
in that the second antenna element operates at frequencies above several tens of MegaHertz.

According to a variant of the invention, the interrogation system operates in the ISM band at 434 MHz.

According to a variant of the invention, the tubular structure comprises a metallic structure in the form of an expandable trellis.

According to a variant of the invention, the sensor is situated on a wall of the tubular structure.

According to a variant of the invention, the biocompatible material is a resin or an elastomer.

According to a variant of the invention, the tubular structure comprises a non-expandable rigid part into which the sensor is integrated.

According to a variant of the invention, the sensor is a pressure sensor comprising at least two resonators, each resonator being coupled to an integrated antenna.

According to a variant of the invention, the antenna element belongs to a metallic tubular structure.

The compactness of the SAW solution and notably at 434 MHz also makes it possible to propose a sensor which makes it possible to measure pressure and temperature while remaining compatible with the bulkiness constraints by considering a structure using three resonators for example. The measurement of the pressure and of the temperature localized at the same point actually makes it possible to significantly improve the precision in the measurement of these parameters According to a variant of the invention, the sensor is a pressure and temperature sensor, comprising a first reference resonator, a second resonator for measuring temperature and a third resonator sensitive to pressure, each resonator being coupled to an integrated antenna.

According to a variant of the invention, the sensor is a pressure and/or temperature sensor, comprising a stack of several substrates each comprising a resonator and an integrated antenna, produced by way of peripheral walls.

According to a variant of the invention, the peripheral walls are of glass paste type.

According to a variant of the invention, the pressure-sensitive resonator is in a head-to-tail position with respect to the reference resonator.

The subject of the invention is also the use of a device according to the invention to measure an arterial pressure and/or a blood temperature characterized in that the expandable structure is placed on a balloon situated at the end of a catheter intended to be introduced into an artery.

The subject of the invention is furthermore a method of fabricating a device according to the invention comprising the following steps:
- the production of an opening on a peripheral part of an expandable tubular structure;
- the placing of said expandable tubular structure on a mandrel exhibiting a groove;
- the positioning of the sensor in the opening of the tubular structure positioned on the mandrel and facing said groove;
- the depositing of a biocompatible shrouding resin making it possible to encapsulate said sensor;
- the removing of the tubular structure from said mandrel.

BRIEF DESCRIPTION OF THE DRAWINGS

The invention will be better understood and other advantages will become apparent on reading the nonlimiting description which follows and by virtue of the appended figures among which.

DETAILED DESCRIPTION

The invention proposes an innovative solution of sensors, wireless and without any battery, allowing notably the measurement of arterial pressure and blood temperature directly implantable in a biological medium, typically in a human artery.

The principle of passive surface wave sensor used in the present invention is described hereinafter. It may according to the known art be notably a temperature and/or pressure sensor.

Generally, a complete system is composed of an interrogation unit (itself consisting of a transmitter part and of a receiver part i.e. T/R) and of an SAW surface acoustic wave temperature and/or pressure sensor. The SAW device is of resonator type thereby making it possible to access structures of reduced sizes. The interrogation system as well as the SAW sensor are furnished respectively with antennas, suitable for the working frequency band (ISM bands 433 MHz, 868 MHz, 2.45 GHz, etc.) or for any other unoccupied frequency band of use, thereby making it possible to perform wireless interrogation of the sensor.

The mode of interrogation is as follows: the transmitter of the interrogation system dispatches an interrogation signal (temporal pulse of a carrier in the ISM band, transmission time slot) to the antenna associated with the SAW resonator. By piezoelectric coupling effect, the incident electromagnetic wave is transformed into an acoustic wave propagating on the surface of the substrate.

If the transmission signal exhibits a resonant frequency sufficiently close to the natural frequency of the SAW resonator, the latter starts resonating while passing through a charge period. Steady state oscillations are then set up at the natural resonant frequency of the SAW device. This resonant frequency is proportional to the speed of the surface wave in the resonant cavity which itself depends on the temperature and the stresses seen by the resonator.

Figure 1:
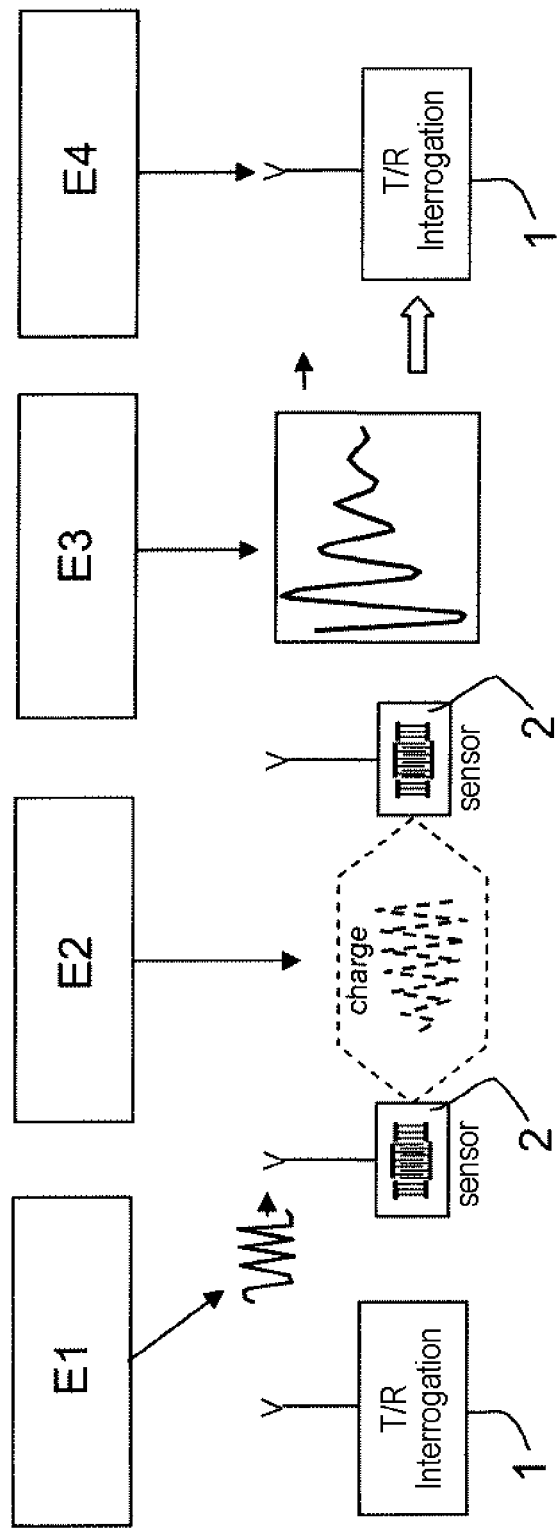
FIG. 1 shows diagrammatically the manner of operation of the device of the invention.

The device of the invention operates in the following manner: the complete system illustrated in FIG. 1 is composed of an interrogation unit 1 (itself consisting of a transmitter part and of a receiver part i.e. T/R) and of the SAW sensor 2 consisting of one or more resonators operating at different frequencies. The interrogation system as well as the SAW sensor are furnished with an antenna suited to the working frequency band thereby making it possible to perform wireless interrogation of the sensor.

The mode of interrogation is as follows: during a first step E1, the transmitter of the interrogation system 1 dispatches an interrogation signal (temporal pulse of a carrier in the frequency band suited to the sensor) to the SAW sensor 2. This pulse exhibits a smaller spectral width than the bandwidth of the resonator.

During a step E2, if the transmission signal exhibits a resonant frequency sufficiently close to the natural frequency of the SAW resonator, the latter starts resonating while passing through a charge period, so as to reach steady state oscillation. This resonant frequency is in particular dependent on the speed of the surface wave in the resonant cavity which depends on the pressure and temperature conditions seen by the resonator.

Undertaken during a step E3 is the reading of the response of the resonator before discharge thereof.

The sensor radiates in its turn (via the antenna which is connected to it) a signal at its resonant frequency which carries the pressure and temperature indication, corresponding to step E4.

The receiver of the interrogation system detects outside of the transmission time slot all or part of the SAW signal (damped oscillation) and extracts therefrom the pressure and/or temperature indication sought via suitable signal processing.

In order to detect the various resonant frequencies of the sensor, a complete scan of the ISM band is performed with a certain frequency increment which is also smaller than the bandwidth of the resonator.

This mode of communication between the interrogator and the sensor makes it possible to obtain interrogation distances of greater than a meter while complying with the radio requirements of the ISM standard.

We shall describe hereinafter in greater detail a sensor used in a device of the invention comprising several surface wave resonators, allowing the measurement of pressure and temperature in situ.

Figure 2:
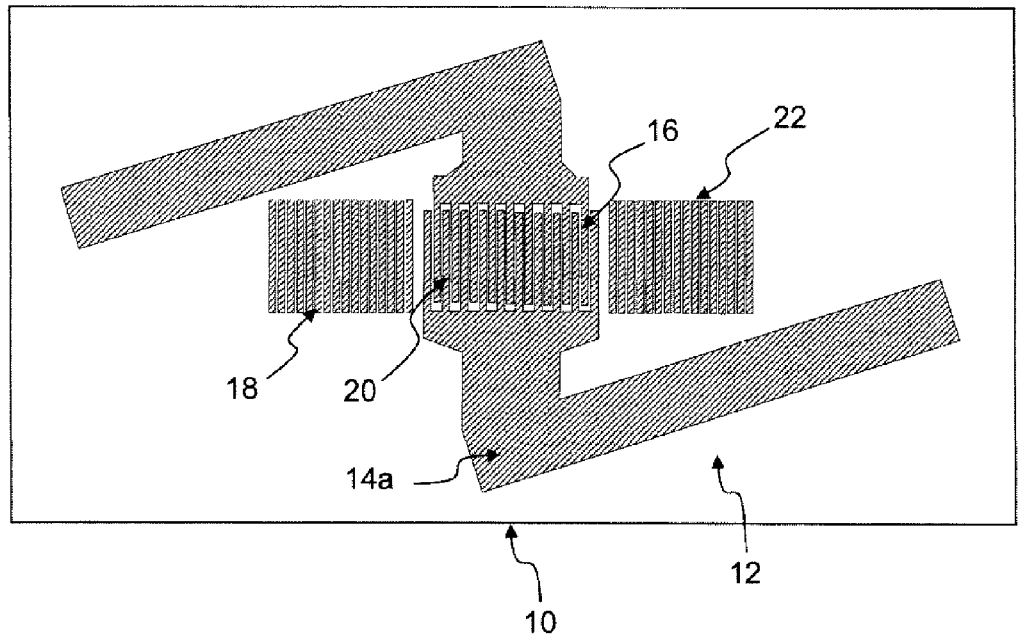
FIG. 2 illustrates a schematic view of a surface wave sensor equipped with antenna strips according to the known art.

FIG. 2 illustrates a schematic view from above of a surface wave sensor 10 consisting of a piezoelectric substrate 12, of a resonant structure, called a resonator, and of two transmission antenna strips 14a. The resonator is composed of a transducer 16 and of two sets of reflectors 18. The piezoelectric substrate 12 may be of quartz, lithium niobate (LiNbO3), lithium tantalate (LiTaO3) or any other piezoelectric material.

The transducer part 16 of the resonator consists of an alternation of metallic electrodes 20, called an interdigital transducer (IDT), alternately connected to the two strips of the antenna 14*a*. The two sets of reflectors 18 consist of an alternation of metallic electrodes 22.

The width of the metallic electrodes 20 of the transducer 16, their spacing, the width of the metallic lines 22 of the sets of reflectors 18, their spacing, their number as well as the type of piezoelectric substrate 12 make it possible to define the resonator's characteristics such as the resonant frequency for example. Thus, each sensor (pressure and temperature) is defined so as to resonate at a particular frequency. The application of a pressure and/or a temperature to the piezoelectric substrate 12 engenders a variation in the resonant frequency of the sensor. The physical parameter is then measured by comparing the frequency of the pressure/temperature resonator with the frequency of a so-called reference resonator. A system of temperature and pressure sensors can advantageously comprise three resonators (pressure, temperature and reference), produced on three different piezoelectric substrates. It is also possible to have two resonators (reference and pressure for example) on the same piezoelectric substrate.

The various metallic elements, namely the metallic electrodes 20 of the transducer 16, the metallic lines 22 of two sets of reflectors 18 and the two antenna strips 14*a*, may be produced by various photolithography technologies, widely known in the field of semiconductors. The metals, as well as their alloys, that can be used to produce these various elements are, for example, aluminum (Al), tungsten (W), platinum (Pt), copper (Cu), titanium (Ti) or any other metal or alloy compatible with photolithography methods and compatible with applications of surface wave resonators.

The production of two antenna strips 14*a* makes it possible to obtain a remotely interrogatable pressure and temperature measurement system. It is important to note that the antenna may be directly integrated with the resonators. In certain cases where the antenna cannot be produced on the piezoelectric substrate, the support corresponding to the tubular structure on which the sensor is fixed can also serve as support for the antenna, if this structure is for example metallic.

A variant of the invention consists in modifying the structure of the tubular structure so that the latter acts as antenna.

Figure 3:
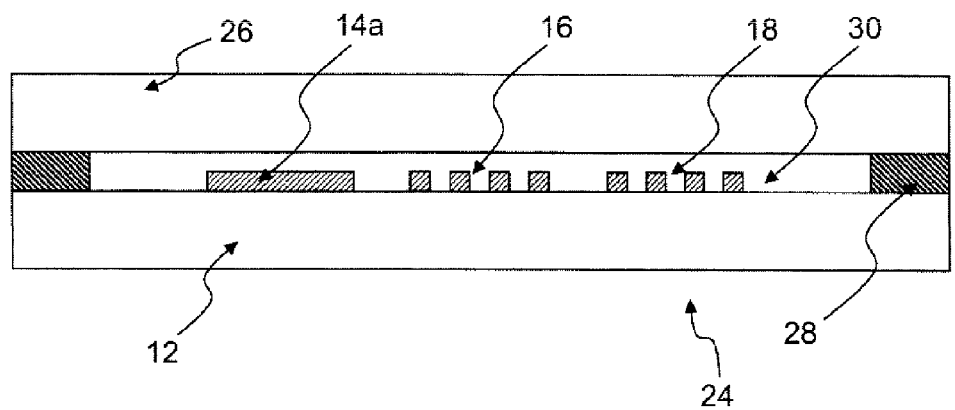
FIG. 3 is a schematic sectional view of a packaged surface wave sensor.

FIG. 3 illustrates a schematic sectional view of a packaged surface wave sensor 24, with a view to implantation in a biological medium.

This packaging is composed of a lid 26 and of walls 28, separating the piezoelectric substrate 12 from the lid 26, thus forming a hermetic cavity 30.

The lid 26 consists of a material with mechanical and dielectric characteristics identical to those of the piezoelectric substrate. In most cases, the material of the lid is the same as the piezoelectric substrate.

The walls 28 are produced by various techniques such as the sintering of sealing paste, previously deposited by silk-screen printing for example. Once the sealing between the lid and the piezoelectric substrate has been carried out, the walls 28 make it possible to ensure a cavity 30 between the two substrates, said cavity being necessary for the propagation of the surface waves. Depending on the applications envisaged, it is possible to vary the pressure inside the cavity. This pressure then serves as reference with respect to the pressure to be measured.

This method of fabrication, carried out in a batch manner, is very widespread in the semiconductor industry and is commonly called MEMS (for Micro-Electro-Mechanical Systems).

Figure 4:
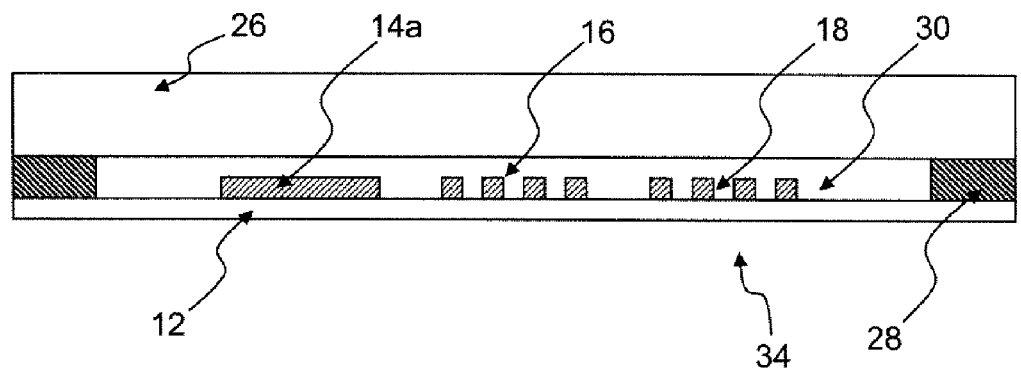
FIG. 4 is a schematic sectional view of a system integrating a pressure sensor with thinned piezoelectric substrate.

FIG. 4 is a schematic sectional view of a system integrating a pressure sensor with thinned piezoelectric substrate 34.

The step of thinning the piezoelectric substrate 12 is mainly carried out on the pressure sensor with a view to obtaining the desired sensitivity to pressure variations. The thinning operation may be carried out in various ways, batch or unitary, such as mechanical polishing, grinding, etching, for example.

This option may also be envisaged for reasons of size reduction with a view to implantation in a biological medium.

Figure 5:
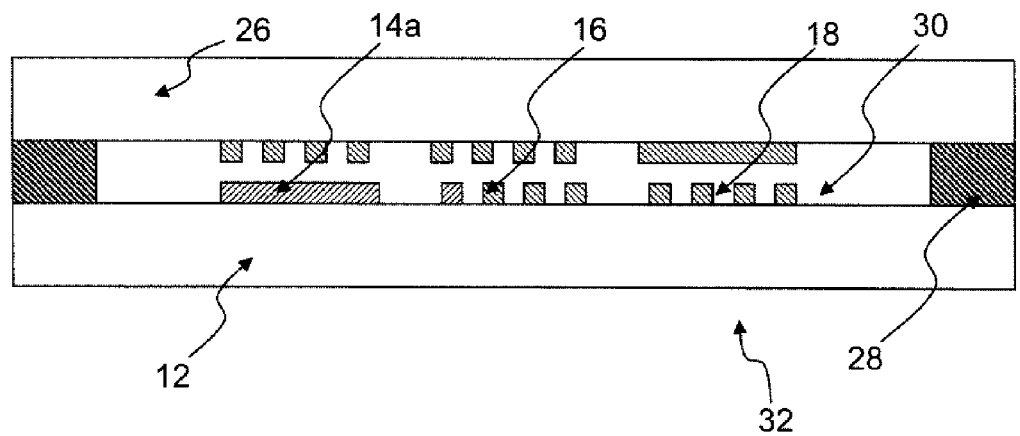
FIG. 5 is a schematic sectional view of a system integrating two surface wave sensors.

FIG. 5 is a schematic sectional view of a system integrating two surface wave sensors 32, positioned head-to-tail. This option may be envisaged for reasons of size reduction with a view to implantation in a biological medium.

The various sensors described above can advantageously be integrated into a device of the invention, and more precisely at the level of a metallic tubular structure of stent type intended notably to be introduced into an artery to measure the arterial pressure thereof.

Figure 6:
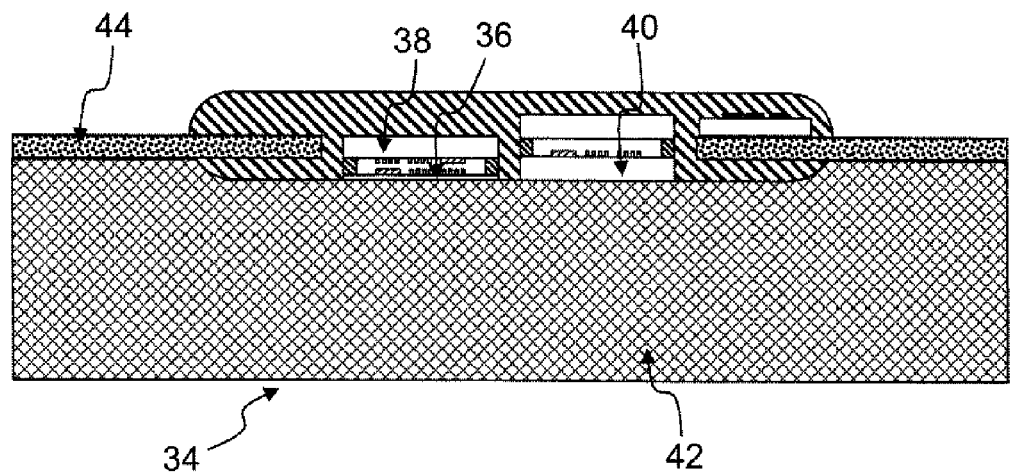
FIG. 6 is a schematic sectional view of an implantable device according to the invention, comprising three surface wave sensors mounted on a biocompatible support.

FIG. 6 illustrates a schematic sectional view of an implantable device according to the invention, comprising three surface wave sensors mounted on a biocompatible support 34. The three sensors used here are a pressure sensor, on a thinned substrate, 36, assembled with the reference sensor 38 and a temperature sensor 40.

These three sensors are positioned/integrated into a metallic stent 42 the particular feature of which is that it has a non-deformable rigid zone 44. The sensors are enveloped in a biocompatible protective resin 46, deposited with the aid of a syringe for example.

Advantageously, a non-integrated antenna is integrated into the stent 42, for example in the rigid zone of the stent 42. This antenna 14*b* can also be enveloped in a biocompatible protective resin 46. An alternative of this variant of the invention consists in making use of the stent 42 as antenna.

It is recalled that, generally, a stent is a small extensible metallic trellis which is slipped into a natural cavity (artery, etc.) to keep it open.

It is essentially used in arteries in the course of an angioplasty (medico-surgical technique for modifying/increasing the diameter of a blood vessel commonly carried out in the case of diseases in which the diameters of the blood vessels are affected (occlusion, stenoses, etc.)).

Nonetheless, since the stent is metallic, and therefore constitutes a metallic foreign body, it can give rise to the occurrence of clotting by platelet aggregation. Medicinal treatments (platelet antiaggregants) are therefore necessary to prevent the occurrence of these problems. In order to reduce the risk of the occurrence of clotting, the stent is protected by a biocompatible resin which partially or entirely envelops the metal.

We shall describe hereinafter an exemplary method of fabricating a device according to the invention intended to be implanted in an artery, the steps of which are illustrated in FIGS. 7*a* to 7*f*.

- initially a rectangular opening 42*a* is produced within the stent 42, allowing the positioning of the sensor. This opening can have dimensions dependent on the location in which it will be placed in the human body;
- the stent is then placed on a mandrel 43 specifically machined to receive the sensors. This machining is composed mainly of a groove 43*a*;
- the SAW-based sensor is then placed in the open zone of the stent by placement performed for example by a method of automated transfer and placement;
- a biocompatible shrouding resin 46 may be deposited with the aid of a syringe or by dipping. The resin is thereafter polymerized under the effect of temperature.

For the measurement of blood pressure, it is important that the encapsulation resin does not spill over onto the face of the sensor which measures the pressure (i.e. the face which is inside the stent).

After polymerization, it is possible to remove the stent without damaging the sensors by supplementing the existing mandrel with a grooved union of slightly greater diameter than that of the mandrel. The elastic characteristics of the stent are used. It is important to note that the bottom of the groove of the union is situated at the same level as the bottom of the groove of the mandrel.

Once the stent has been removed from the union, it is ready to be used with a view to implantation and notably within the realm of angioplasty.

Figure 8:
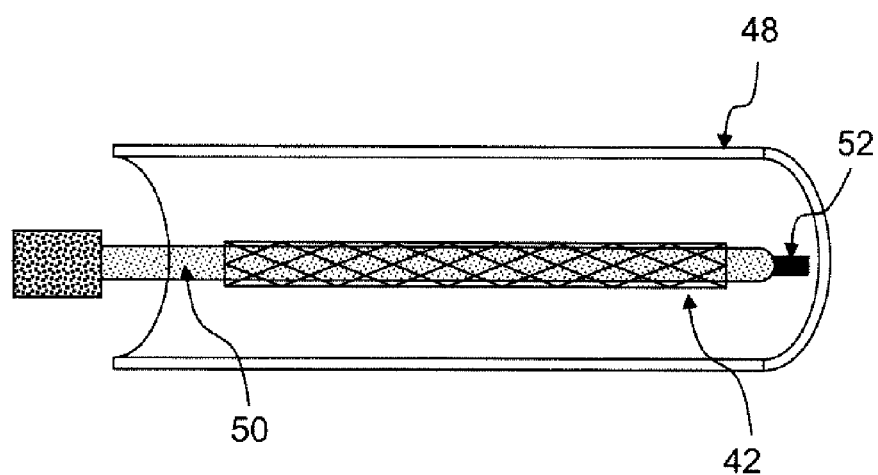
FIGS. 8, 9 and 10 are schematic sectional views of various steps of placing a device of the invention within an artery.
Figure 7A:
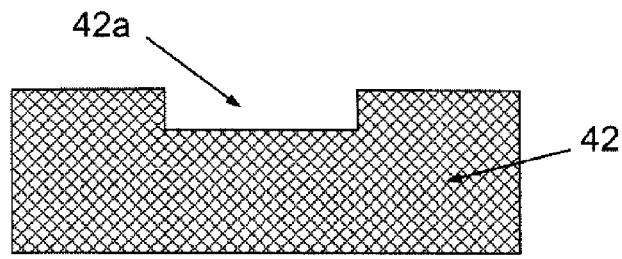
FIGS. 7a to 7f illustrate the various steps of an exemplary method of fabricating a device of the invention.
Figure 7B:
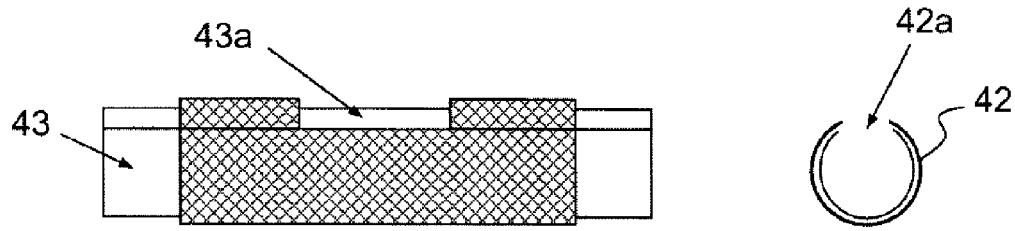
Figure 7C:
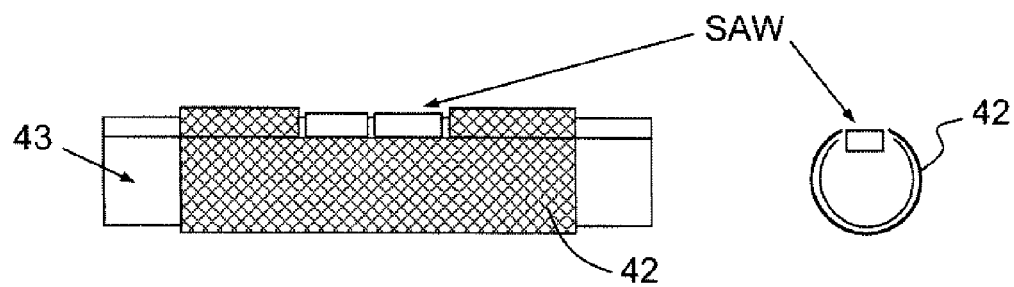
Figure 7D:
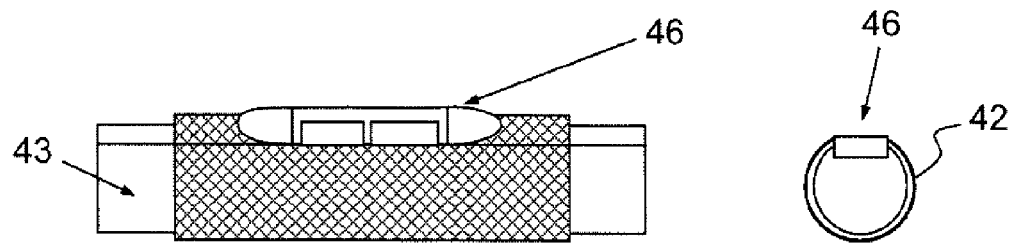
Figure 7E:
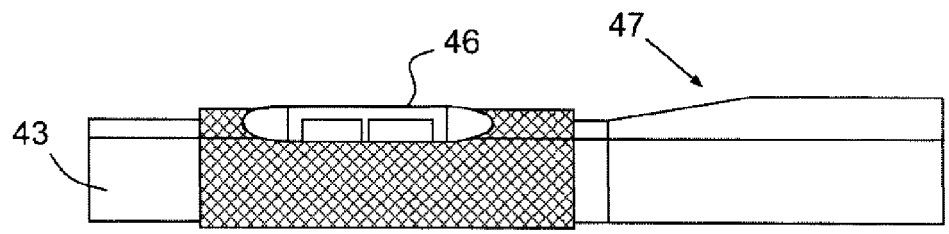
Figure 7F:
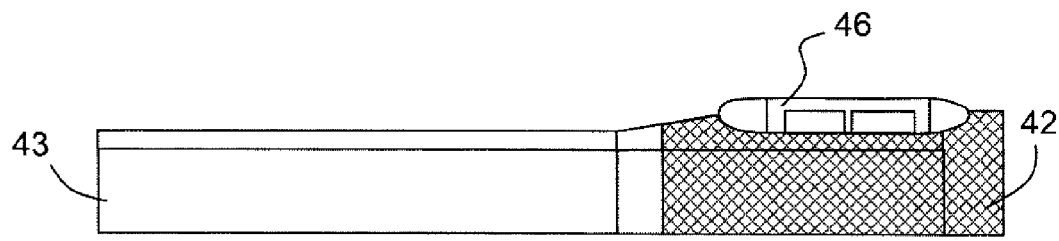
Figure 9:
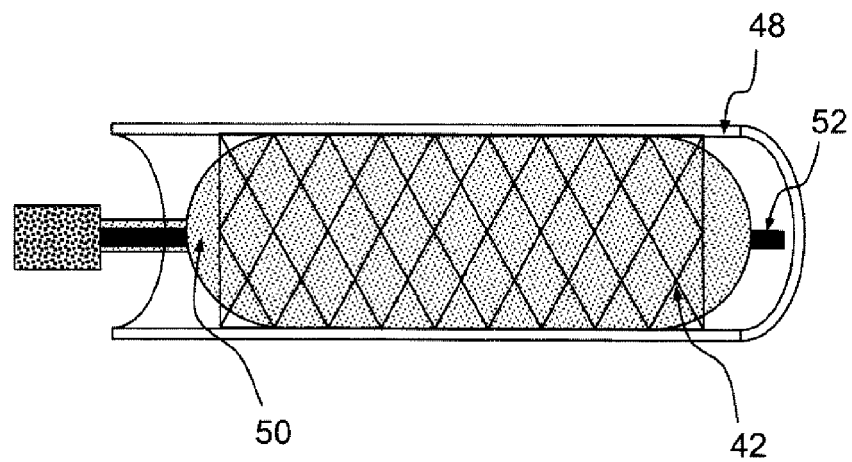
Figure 10:
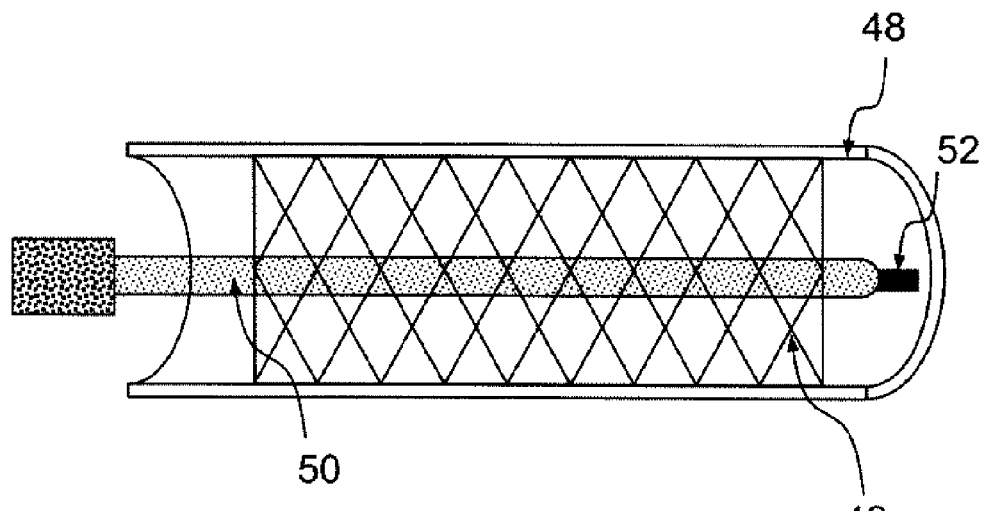

FIG. 8, FIG. 9 and FIG. 10 are schematic sectional views of the steps of putting a stent 42 into place once it has been produced with a view to the aforementioned applications.

First of all, the stent is fitted on a deflated balloon 50 situated at the extremity of a catheter 52 (FIG. 8). The catheter is thereafter introduced into the artery 48. The balloon 50 is thereafter inflated (FIG. 9), thereby giving rise to an expansion of the stent 42 which then sticks to the wall of the artery 48. The balloon 50 is thereafter deflated (FIG. 10) and the catheter removed 52.

Figure 11:
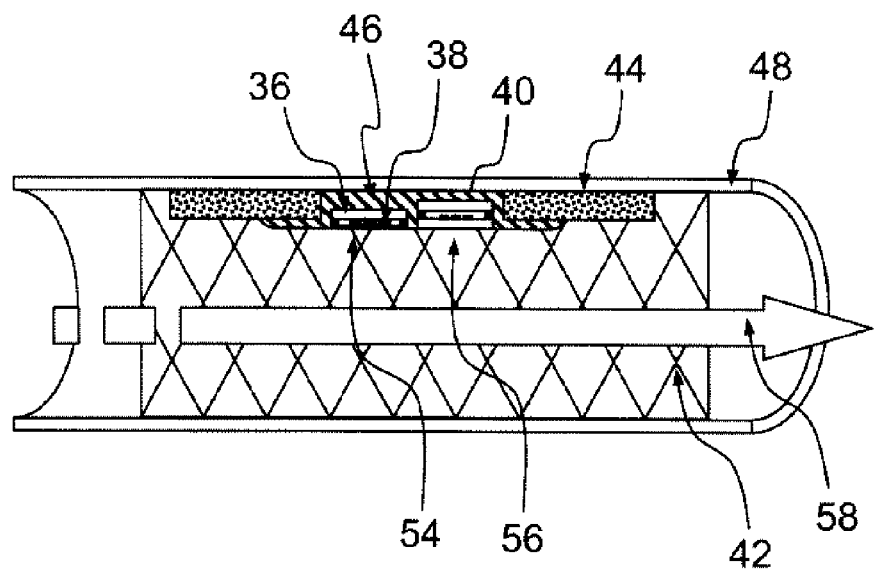
FIG. 11 illustrates a schematic sectional view of a device according to the invention implanted in an artery.

FIG. 11 illustrates a schematic sectional view of the device of the invention, implanted at the level of an artery 48. The sensors are placed against the wall of the artery 48. The surface 54 of the pressure sensor 36, previously thinned surface, and the surface 56 of the temperature sensor 40 are directly in contact with the blood stream flowing through the artery 58, allowing measurement of the arterial pressure and the blood temperature. The positioning of the sensors in a rigid (that is to say non-deformable) zone of the stent makes it possible to avoid the problems of detachment of the resin from the stent 42 during the operation of inflating the balloon 50.

It should be noted that the resin for biocompatible and hermetic encapsulation is chosen to be sufficiently rigid to prevent the sensor from becoming detached from the stent when the balloon is inflated and then deflated during installation.

The invention claimed is:

1. A remotely interrogatable pressure and/or temperature measuring device comprising at least:
   an acoustic wave sensor comprising at least one resonator coupled to a first antenna element; and
   an interrogation system comprising a second antenna element for transmission and reception,
   wherein the measuring device further comprises an expandable tubular structure, said structure integrating a biocompatible material and said acoustic wave sensor encapsulated in the biocompatible material and in that the second antenna element operates at frequencies above several tens of MegaHertz, and
   wherein the tubular structure comprises a metallic structure in the form of an expandable trellis.

2. The remotely interrogatable pressure and/or temperature measuring device as claimed in claim 1, wherein the sensor is situated on an internal wall of the expandable tubular structure.

3. The remotely interrogatable pressure and/or temperature measuring device as claimed in claim 1, wherein the biocompatible material is a resin.

4. The remotely interrogatable pressure and/or temperature measuring device as claimed in claim 1, wherein the expandable tubular structure comprises a non-expandable rigid part into which the sensor is integrated.

5. The remotely interrogatable pressure and/or temperature measuring device as claimed in claim 1, wherein the sensor is a pressure sensor comprising at least two resonators, each resonator being coupled to an integrated antenna.

6. The remotely interrogatable pressure and/or temperature measuring device as claimed in claim 1, wherein the sensor is a pressure and temperature sensor, comprising a first reference resonator, a second resonator for measuring temperature and a third resonator sensitive to pressure, each resonator being coupled to an integrated antenna.

7. The remotely interrogatable pressure and/or temperature measuring device as claimed in claim 1, wherein the interrogation system operates in an ISM band at 434 MHz.

8. The remotely interrogatable pressure and/or temperature measuring device as claimed in claim 1, wherein the sensor is situated on an internal wall of the expandable tubular structure.

9. The remotely interrogatable pressure and/or temperature measuring device as claimed in claim 1, wherein the biocompatible material is a resin.

10. The remotely interrogatable pressure and/or temperature measuring device as claimed in claim 1, wherein the expandable tubular structure comprises a non-expandable rigid part into which the sensor is integrated.

11. The remotely interrogatable pressure and/or temperature measuring device as claimed in claim 1, wherein the sensor is a pressure sensor comprising at least two resonators, each resonator being coupled to an integrated antenna.

12. The remotely interrogatable pressure and/or temperature measuring device as claimed in claim 1, wherein the sensor is a pressure and temperature sensor, comprising a first reference resonator, a second resonator for measuring temperature, and a third resonator sensitive to pressure, each resonator being coupled to an integrated antenna.

13. The remotely interrogatable pressure and/or temperature measuring device as claimed in claim 1, wherein the sensor is a pressure and/or temperature sensor, comprising a stack of several substrates each comprising a resonator and an integrated antenna, produced by way of peripheral walls.

14. The remotely interrogatable pressure and/or temperature measuring device as claimed in claim 13, wherein the at least one resonator is in an upper position in the stack and in a head-to-tail position with respect to a reference resonator.

15. A method of fabricating a measuring device as claimed in claim 1, comprising the following steps:
   producing an opening on a peripheral part of the expandable tubular structure;
   placing said expandable tubular structure on a mandrel exhibiting a groove;
   positioning the sensor in the opening of the expandable tubular structure positioned on the mandrel and facing said groove;
   depositing a biocompatible shrouding resin encapsulating said sensor; and
   removing the expandable tubular structure from said mandrel.

16. A remotely interrogatable pressure and/or temperature measuring device, comprising:
   an acoustic wave sensor comprising at least one resonator coupled to a first antenna element; and
   an interrogation system comprising a second antenna element for transmission and reception,
   wherein the measuring device further comprises an expandable tubular structure, said structure integrating a biocompatible material and said acoustic wave sensor encapsulated in the biocompatible material and in that the second antenna element operates at frequencies above several tens of MegaHertz, and wherein the sensor is a pressure and/or temperature sensor, comprising a stack of several substrates each comprising a resonator and an integrated antenna, produced by way of peripheral walls.

17. The remotely interrogatable pressure and/or temperature measuring device as claimed in claim 16, wherein the peripheral walls are of a glass paste.

18. The remotely interrogatable pressure and/or temperature measuring device as claimed in claim 16, wherein the resonator is in an upper position in the stack and in a head-to-tail position with respect to a reference resonator.

19. A remotely interrogatable pressure and/or temperature measuring device comprising at least:
   an acoustic wave sensor comprising at least one resonator coupled to a first antenna element; and
   an interrogation system comprising a second antenna element for transmission and reception,
   wherein the measuring device further comprises an expandable tubular structure, said structure integrating a biocompatible material and said acoustic wave sensor encapsulated in the biocompatible material and in that the second antenna element operates at frequencies above several tens of MegaHertz, and
   wherein a method of fabricating the measuring device comprises the following steps:
   producing an opening on a peripheral part of the expandable tubular structure;
   placing said expandable tubular structure on a mandrel exhibiting a groove;
   positioning the sensor in the opening of the expandable tubular structure positioned on the mandrel and facing said groove;
   depositing a biocompatible shrouding resin making it possible to encapsulate said sensor; and
   removing the expandable tubular structure from said mandrel.

* * * * *